US006333355B2

(12) United States Patent
Sembo et al.

(10) Patent No.: US 6,333,355 B2
(45) Date of Patent: *Dec. 25, 2001

(54) METHOD TO CONTROL ANIMAL ECTO-PARASITES

(75) Inventors: Satoshi Sembo, Takarazuka; Tatsuya Mori; Noriyasu Sakamoto, both of Toyonaka, all of (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,499

(22) Filed: Nov. 17, 1998

(30) Foreign Application Priority Data

Nov. 20, 1997 (JP) .................................................... 9-319503

(51) Int. Cl.⁷ ...................................................... A61K 31/17

(52) U.S. Cl. .............................................................. 514/594
(58) Field of Search ............................................... 514/594

(56) References Cited

FOREIGN PATENT DOCUMENTS

| 030605 5A | 3/1989 | (EP) . |
| 031878 2A | 6/1989 | (EP) . |
| 033760 0A | 10/1989 | (EP) . |
| 042544 3A | 5/1991 | (EP) . |
| 337600 A2 | * 10/1989 | (JP) . |

* cited by examiner

*Primary Examiner*—Dwayne C. Jones
(74) *Attorney, Agent, or Firm*—Birch, Stewart, Kolasch & Birch, LLP

(57) ABSTRACT

The present invention provides a method to control ecto-parasites of a host animals wherein 1-(2,6-difluorobenzoyl)-3-[2-fluoro-4-(1,1,2,3,3,3-hexafluoropropoxy)phenyl]urea is applied to the said host animals.

By the method of the present invention, ecto-parasites of animals can be controlled effectively for a long period of time.

12 Claims, No Drawings

METHOD TO CONTROL ANIMAL ECTO-PARASITES

BACKGROUND OF THE INVENTION

The present invention relates to a method for controlling ecto-parasites of animals. In detail, the present invention relates to a method for controlling ecto parasites of animals wherein 1-(2,6-difluorobenzoyl)-3 -[2-fluoro-4-(1,1,2,3,3,3-hexafluoropropoxy)phenyl]urea (hereinafter, recited as Compound #1) is applied to the said animals.

Ecto-parasites have-been responsible for the transmission of disease. Fleas have been a particular problem because of their ability to completely infest an environment. The female flea lays her eggs on the host animal after mating. The eggs are able to fall off the host and be distributed to the host's environment. By this mechanism, the eggs are able to cover a larger area.

It is disclosed in Japanese patent publication (laid-open) No. 2-138247 that Compound #1 has an insecticidal activity. The publication discloses that benzoylurea compounds including Compound #1 in the publication are excreted as they are and therefore, can control the larvae and eggs of such insects like houseflies that breed in the excretion of domestic animals when they are applied to the domestic animals orally.

It is disclosed in U.S. Pat. No. 4,089,975 that benzoylurea compounds such as 1-(2,6-difluorobenzoyl)-3 (4-trifluoromethoxyphenyl)urea (hereinafter, recited as Compound A) and 1-(2,6-difluorobenzoyl)-3-[4-(1,1,2,2-tetrafluoroethoxy)phenyl]urea (hereinafter, recited as Compound B) can also be used for controlling insects which inhabit in excretion of domestic animals.

On the other hand, Japanese patent publication (laid-open) No. 63-72631 discloses a method for defending dogs or cats from re-infection of fleas by applying juvenile hormone like chemical compounds, triazine derivatives that regulate the growth of fleas and benzoylurea derivatives (specifically, N-3-(5-trifluoromethylpyridin-2-yl)phenyl-N'-benzoylurea derivatives) that regulate the growth of fleas to dogs or cats. However, the effectiveness of the method generally do not last a sufficient amount of time.

SUMMARY OF THE INVENTION

The present invention relates to a method for systemic control of ecto-parasites of animals.

More specifically, the present invention relates to a method that effectively controls ecto-parasites for a comparably long period of time by applying Compound #1 to the host animal. The propagation of ecto-parasites is prevented by applying an effective amount of Compound #1 to the host animal and letting the ecto-parasites feed thereon.

DETAILED DESCRIPTION OF THE INVENTION

Compound #1, employed in the present invention, may be produced by employing Japanese patent publication (laid-open) No. 2-138247 (recited above).

The objective ecto-parasites of the present invention are pests that live externally to the host animal but necessitate blood from the host animal to achieve normal reproductive abilities. More specifically, the objective ecto-parasites of the present invention are not only limited to the kinds of mites and/or ticks (Acarina) such as *Boophilus microplus* and *Haemaphxalis longicornis*; Pulicidae (fleas) such as *Ctenocephalides felis* (cat fleas), *Ctenocephalides canis* (dog fleas), and *Xenopsylla cheopis*; and Anoplura (lice) such as *Haematopinus eurysternus* and *Damalinia ovis* that live external to the host organism but, may include blood sucking Dipthera insects such as *Tabanus chrysurus, Culicoides oxystoma*, and *Simulium iwatens*.

The objective host animals for the present invention are warm-blooded animals whose blood will permit an ecto-parasite to achieve normal reproductive capabilities. More specifically, the objective host animals include pet animals such as dogs, cats, mice, rats, hamsters, squirrels, rabbits, ferrets, and birds (for example, pigeons, parrots, minas, java sparrows, love birds, and canaries) but, are not limited to the kinds of domestic animals such as cattle, horses, swine, sheep, ducks, drakes, and poultry.

The manner which Compound #1 is administered as an efficacious dosage may vary. Compound #1 may be administered to the host animals at a rate from about 0.01 mg to about 1000 mg per each kilogram of the host animal (i.e. 0.01–1000 mg of Composition #1/kg of the host animal), and preferably at the rate from about 0.1 mg to about 500 mg per each kilogram of the host animal (i.e., 0.1–500 mg Composition #1/kg of the host animal). The preferred dosage for controlling a given ecto-parasite is determined individually, but it is generally necessary to have an efficacious amount of Compound #1 present in the bloodstream of the treated host animal to control the given ecto-parasite. The systemic control of ecto-parasites is achieved by having the ecto-parasites ingest blood from the treated host animal so that the said ecto-parasite is exposed to an efficacious amount of Compound #1. As used herein, "efficacious amount" means an amount that leads to a reduced rate of the hatching of eggs and/or to the inability to fertilize.

Compound #1 is may be applied in pure form, but preferably in the form of a composition which comprises Compound #1 in an amount of 0.1% to 99% by weight in the composition.

Compound #1 may be applied to host animals by oral or non-oral application.

In oral application, examples of the form of the composition includes tablets, liquids, capsules, wafers, biscuits, emulsifiable concentrates, and/or so on. The oral application includes a method to apply the composition and a method to apply the mixture of Compound #1 or the composition with feed for the host animals. To prevent hydrolysis or degradation by constituents of animal feed, Compound #1 may previously be formulated in a protective matrix such as gelatin, and be further protected by formulation with preservatives and anti-oxidants such as sodium benzoate, parabens, BHT (butylated hydroxytoluene), and BHA (butylated hydroxyanisole).

In non-oral application, examples of the form of the composition includes a water soluble suspension, oily suspension, implants comprising of resins and soluble/erodible materials and/or so on. The non-oral application includes parenteral applications such as subcutaneous, intravenous, and intramuscular injection; percutaneous applications such as spot-on and pour-on application; implants application.

The tablet formulation for oral application generally employs sugars such as lactoses, sucroses, mannitols, and sorbitols; excipien agents such as celluloses and calcium phosphates; binders such as powdered starches, gelatins, gum arabic, tragacanth, methylcelluloses, agars, alginic acids, and alginic acid salts; lubricants such as silicas, talcs, stearic acids, and stearic acid salts; Dragee cores such as polyvinyl pyrrolidones, polyethylene glycols, and titanium dioxides; and/or so on in addition to Compound #1. Coloring agents and food additives may also be employed when necessary.

The capsule formulation for oral application may be a dry-filled capsule comprising of gelatins, a soft capsule comprising of gelatins and plasticisers such as glycerins, sorbitols, and so on. The said dry-filled capsule, may include excipien agents such as lactoses, binders such as powdered starches, lubricants such as talc and stearic acid salts, stabilizers, and so on. The soft capsule formulation generally comprises. Compound #1 dissolved or suspended in a suitable solvent such as fatty oils, parraffin oils, liquid polyethylene glycols, and so on. In addition, the soft capsule formulation may also comprise of a stabilizer when necessary.

The composition for a non-orally applied injection may be water-soluble suspensions or oily suspensions which comprise animal/plant oils such as sesame oils; esters of fatty acids such as ethyl oleates; triglycerides; thicking agent such as sodium carboxymethylcellulose, sorbitol, and dextran; and so on in addition to Compound #1.

The composition for percutaneous application may be a spot-on formulation or a pour-on formulation which comprises Compound #1 dissolved or suspended in esters such as polyoxyethylene hardened castor oil, esters of stearic acid, fatty acid coconut oil diethanolamide, methyl oleate and ethyl oleate; fatty acids such as lauric acid and oleic acid; alcohols such as myristyl alcohol, palmityl alcohol and polyoxyethylene polyoxypropylene glycol; ethers such as dipropyleneglycol monomethyl ether; and/or so on.

EXAMPLES

Hereinafter, the present invention is explained more specifically with the examples and is compared to Compound A disclosed in U.S. Pat. No. 4,089,975; Compound B, also disclosed in U.S. Pat. No. 4,089,975; and 1-(2,6-difluorobenzoyl)-3-[3-(3-chloro-5-trifluoromethylpyridin-2-yloxy)phenyl]urea (hereinafter, recited as Compound C), disclosed in Japanese patent publication (laid-open) 63-72631, but does not limit the present invention in any way.

TABLE 1

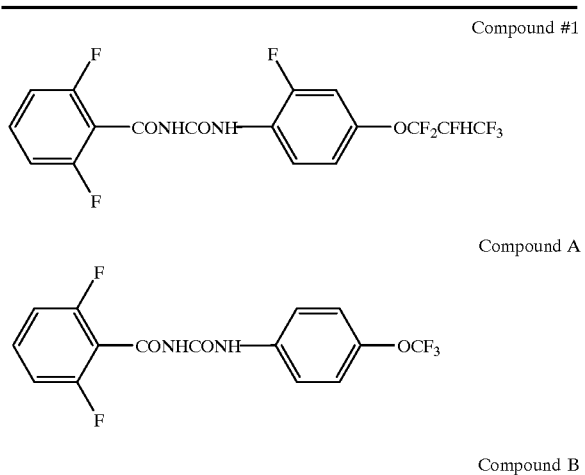

Compound #1

Compound A

Compound B

TABLE 1-continued

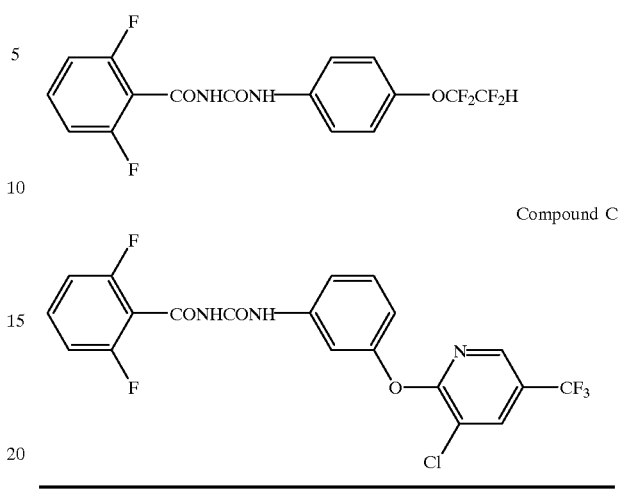

Compound C

Example 1

An each predetermined amount of Compound #1, Compound A, Compound B and Compound C was dissolved in corn oil to be a composition so that a dose of 20 milligrams per kilogram body weight of the mouse would ultimately be applied. By using an appropriate sonde for the mouse, oral application to the mouse was performed at the rate of about 10 mL of the composition per kilogram body weight of the mouse. The said mouse was then stabilized with a wire netting, and was placed in a plastic container (depth 15 cm×width 15 cm×height 60 cm). Thirty (10 male and 20 female) starved adult cat fleas (*Ctenocephalides felis*) were freed into the said plastic container and the produced flea eggs were retrieved five days later. A suitable amount (about 60 eggs) was transferred to a plastic dish and, preserved under the conditions wherein the temperature was 26° C. and the humidity was at 90%. After 2 days of preservation, the hatching conditions were observed.

Afterwards, the treated mouse was allowed to inhabit a standard pet cage with food and water. Ten days after the application, the mouse was stabilized, placed in a plastic container, and was exposed to cat fleas in the same way as stated above. The produced flea eggs were then retrieved 14 days after the application, preserved in the conditions stated above and had the hatching conditions observed.

Twenty-six days after the application, the mouse was stabilized, placed in a plastic container, and was exposed to cat fleas in the same way as stated above. The produced flea eggs were then retrieved 30 days after the application of the composition, preserved in the conditions stated above, and had the hatching conditions observed.

The same procedure was repeated without the application of the composition.

The percentages of hatching for applied mouse "T" and the percentage of hatching for non-applied mouse "C" were derived from the equation, respectively:

T=(the amount of hatched eggs)÷(the amount of retrieved eggs)× 100

C=(the amount of hatched eggs)÷(the amount of retrieved eggs)× 100

The acquired values of "T" and "C" were used to determine the adjusted percentage concerning the loss of hatchings by employing equation 1.

The results are given in table 2.

Equation 1

The acquired values of "T" and "C" were utilized in the following equation:

The adjusted percentage concerning the loss of hatchings (%)=(C−T)÷C×100 to determine the adjusted percentage concerning the loss of hatchings (hereinafter, recited as APH). As used herein, "APH" is the adjusted comparison between "T" and "C" which measures the effect Compound #1 was able to enforce upon a given group of retrieved eggs. In other words, "APH" looks at the amount of eggs that were unable to hatch rather than the amount of eggs that were able to hatch.

TABLE 2

| | Application amount | adjusted percentage concerning the loss of hatchings (%) | | |
|---|---|---|---|---|
| | (mg/kg) | 5 days after | 14 days after | 30 days after |
| Compound #1 | 20 | 100 | 100 | 93 |
| Compound A | 20 | 0 | 0 | |
| Compound B | 20 | 83 | 0 | |
| Compound C | 20 | 96 | 77 | 11 |

As given in the results of the table above, it was not effective for this method to control fleas with the aid of blood of mouse by using Compound A and Compound B which were used for method to control housefly larvae and the like living in excretions of domestic animals by applying to the domestic animals as disclosed in U.S. Pat. No. 4,089,975. In addition, it was effective to the flea eggs 5 days after production but, was not effective to the flea eggs 30 days after production for this method by using Compound C which was usable for preventing re-infection of fleas by applying to dogs and cats as disclosed in Japanese patent publication (laid-open) No. 63-72631. To the contrary, Compound #1 used for the method of the present invention, which was disclosed in Japanese patent publication (laid-open) No. 2-138247 to be usable for the method to control housefly larvae and the like living in excretion of domestic animals by applying to the domestic animals (said method was a similar method disclosed in U.S. Pat. No. 4,089,975), showed an extraordinary inhibition of hatchings such flea eggs that are not only 5 days but 30 days after production.

Example 2

Each of four cats (a cross between the Abyssinian cat and the European type household cat; weight, about 2.2–2.9 kg) was infested with 100 adult cat fleas (*Ctenocephalides felis*) and then was placed in a steel cage wherein the steel cage comprised of a removable bottom tray, had the dimensions of 760 mm (width)×540 mm (depth)×610 mm (height), and had a supply of solid feed and water. Seven days after infestation, the weights of two cats of were measured and Compound #1 was applied orally to each of said two cats in an amount of 20 mg per one kilogram of the weight of the cat by incorporating Compound #1 into cat feed and having the cat to eat it. After application, the cats were placed in said steel cages.

The flea eggs collected onto the removable bottom tray were retrieved 6 and 14 days after the date of application. About 60 eggs were chosen from each batch of retrieved eggs. They were transferred to a plastic dish and then preserved under the conditions wherein the temperature was 26° C. and the humidity was at 90%. After 5–7 days of preservation, the eggs were observed about hatching.

The same procedure was repeated with another two cats except that cat feed comprising no Compound #1 was applied.

The percentages of hatching for applied cats "T" and the percentage of hatching for non-applied cats "C" were derived from the equation, respectively:

T=(the amount of hatched eggs)÷(the amount of retrieved eggs)×100

C=(the amount of hatched eggs)÷(the amount of retrieved eggs)×100

The obtained values of "T" and "C" were then used to determine the APH by employing the equation 1 mentioned above Example 1.

The average APH for Compound #1 was 81.9% after 6 days and was 79.6% after 14 days.

Example 3

Each of six dogs (beagle dog; weight, 9–10 kg) was infested with 100 adult cat fleas (*Ctenocephalides felis*) and then was placed in a steel cage comprised of a removable bottom tray, had the dimensions of 760 mm (width)×540 mm (depth)×610 mm (height), and had a supply of solid feed on the market and water one day after infestation, the weights of three dogs were measured and Compound #1 was applied orally to each of said three dogs in an amount of 10 mg per one kilogram of the weight of the dog by incorporating Compound #1 into dog feed and having the dog to eat it. After application, the dogs were placed in said steel cages.

The flea eggs collected onto the removable bottom tray were retrieved 4 and 5 days after the application. About 60 eggs were chosen from each batch of retrieved eggs. They were transferred to a plastic dish and then preserved under the conditions wherein the temperature was 26° C. and the humidity was at 90%. After 5–7 days of preservation, the eggs were observed about hatching.

The same procedure was repeated with another three dogs except that dog feed comprising no Compound #1 was applied. The percentages of hatching for applied dogs "T" and the percentage of hatching for non-applied dogs "C" were derived from the equation, respectively:

T=(the amount of hatched eggs)÷(the amount of retrieved eggs)×100

C=(the amount of hatched eggs)÷(the amount of retrieved eggs)×100

The obtained values of "T" and "C" were then used to determine the APH by employing the equation 1 mentioned above Example 1.

The average APH was 86.5% after 4 days and was 76.6% after 5 days.

Compound #1 was disclosed in Japanese patent publication (laid-open) No. 2-138247 as a compound that can control insects breeding in excretion but, was also able to exceed the effectiveness of Compound A, B, and C when employed in a systemic method. Table 1 exhibits the superior effectiveness Compound #1 sets forth on the $30^{th}$ day after application. Compounds A and B could not exhibit any effectiveness past the $14^{th}$ day after application and Compound C was only able to exhibit a low 11% APH on the $30^{th}$ day after application. Compound #1 showed its superior effectiveness by being able to provide 93% APH on the 30$^{th}$ day.

In addition, Compound #1 was able to provide exceptional results when applied to a cat or dog. The cat had a surprisingly high APH of 80% on the 14$^{th}$ day after application while the dog was also able to provide high APH of 77% on the 5$^{th}$ day after application.

Compound A and Compound B are disclosed in U.S. Pat. No. 4,089,975 as a compound that controls excretion-breeding insects but, neither Compound A nor Compound B effectively control ecto-parasites when employed in a systemic method. Compound C is disclosed in Japanese Laid-open Patent No. sho63-72631-A as a compound that avoids re-infection by being applied to cats or dogs but, was not effective against flea eggs 30 days after application. The present invention was effective after a long period of time when employed in a systemic method.

What is claimed is:

1. The method to systemically control ecto-parasites of host animals through the host animal blood wherein a systemically effective amount of 1-(2,6-difluorobenzoyl)-3-(2-fluoro-4-(1,1,2,3,3,3-hexafluoropropoxy)phenyl)urea is applied to the said host animals.

2. The method according to claim 1, wherein the amount of 1-(2,6-difluorobenzoyl)-3-[2-fluoro-4-(1,1,2,3,3,3-hexafluoropropoxy)phenyl]urea applied to the host animals is from 0.1 mg to 500 mg per 1 kg of the host animals.

3. The method according to claim 1 or 2, wherein the host animals are pets.

4. The method according to claim 2, wherein the animals are pets.

5. The method according to claim 4, wherein the animals are pets selected from cats or dogs.

6. The method according to claim 1, wherein the amount of 1-(2,6-difluorobenzoyl)-3[2-fluoro-4-(1,1,2,3,3,3-hexafluoropropoxy)phenyl]urea applied to the host organism is from 0.01 mg to 1000 mg per 1 kg of the host animals.

7. The method according to claims 1 or 2, wherein the 1-(2,6-difluorbenzoyl)-3-[2-fluoro-4-(1,1,2,3,3,3-hexafluoropropoxy)phenyl]urea is applied by non-oral application.

8. The method according to claim 7, wherein the non-oral application is selected from the group consisting of parenteral applications, percutaneous applications, and implants application.

9. A method to inhibit flea eggs produced on host animals from hatching wherein 1-(2,6-difluorobenzoyl)-3-[2-fluoro-4-(1,1,2,3,3,3-hexafluoropropoxy)phenyl]urea is applied to the said host animals.

10. The method according to claim 9, wherein the amount of 1-(2,6-difluorobenzoyl)-3-[2-fluoro-4(1,1,2,3,3,3-hexafluoropropoxy)phenyl]urea applied to the host organism is from 0.01 mg to 1000 mg per 1 kg of the host animals.

11. The method to systemically control ecto-parasites of warm-blooded animals which comprises applying a systemically effective amount of 1-(2,6-difluorobenzoyl)-3-(2-fluoro-4-(1,1,2,3,3,3-hexafluoropropoxy)phenyl)urea to the animals and letting the ecto-parasites feed thereon.

12. The method to systemically control ecto-parasites of warm-blooded animals which comprises applying a systemically effective amount of 1-(2,6-difluorobenzoyl)-3-(2-fluoro-4-(1,1,2,3,3,3-hexafluoropropoxy)phenyl)urea to the animals and having the ecto-parasites ingest blood from the animals so that the ecto-parasite is exposed to an efficacious amount of the 1-(2,6-difluorobenzoyl)-3-(2-fluoro-4-(1,1,2,3,3,3-hexafluoropropoxy)phenyl)urea.

* * * * *